United States Patent
Yoshikawa et al.

(10) Patent No.: US 9,506,940 B2
(45) Date of Patent: Nov. 29, 2016

(54) AUTOMATIC ANALYSIS APPARATUS

(71) Applicant: HITACHI HIGH-TECHNOLOGIES CORPORATION, Tokyo (JP)

(72) Inventors: Keiko Yoshikawa, Tokyo (JP); Akihisa Makino, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/402,416

(22) PCT Filed: May 24, 2013

(86) PCT No.: PCT/JP2013/064427
§ 371 (c)(1),
(2) Date: Nov. 20, 2014

(87) PCT Pub. No.: WO2013/183459
PCT Pub. Date: Dec. 12, 2013

(65) Prior Publication Data
US 2015/0147230 A1   May 28, 2015

(30) Foreign Application Priority Data
Jun. 4, 2012  (JP) .................. 2012-126668

(51) Int. Cl.
*G01N 35/02* (2006.01)
*G01N 21/51* (2006.01)
(Continued)

(52) U.S. Cl.
CPC ............ *G01N 35/025* (2013.01); *G01N 21/49* (2013.01); *G01N 21/51* (2013.01); *G01N 21/82* (2013.01); *G01N 33/86* (2013.01); *G01N 35/0099* (2013.01); *G01N 35/02* (2013.01); *G01N 21/253* (2013.01); *G01N 2015/0693* (2013.01);
(Continued)

(58) Field of Classification Search
CPC ... G01N 33/86; G01N 33/4905; G01N 21/27
See application file for complete search history.

(56) References Cited

U.S. PATENT DOCUMENTS 4,363,245 A * 12/1982 Schmid .................. G01N 35/04
198/724
5,290,513 A * 3/1994 Berthold ................ G01N 21/76
250/328
(Continued)

FOREIGN PATENT DOCUMENTS

JP   59-028642 A   2/1984
JP   63-191962 A   8/1988
(Continued)

OTHER PUBLICATIONS

Chinese Office Action received in corresponding Chinese Application No. 201380027466.4 dated Aug. 5, 2015.

*Primary Examiner* — Neil N Turk
*Assistant Examiner* — Matthew Krcha
(74) *Attorney, Agent, or Firm* — Mattingly & Malur, PC

(57) ABSTRACT

A configuration of detecting light from the front face of a light source is the best for confirming the variation of a light quantity, but when a plurality of light sources are present, as many detectors for checking a light quantity as the light sources are necessary and the apparatus configuration becomes complex. In the present invention, a detector for checking a light source light quantity is installed in a reaction container transfer mechanism used commonly for a plurality of detection sections, and the light quantities of light sources are checked with the detector.

11 Claims, 2 Drawing Sheets

(51) Int. Cl.
    *G01N 35/00*     (2006.01)
    *G01N 21/49*     (2006.01)
    *G01N 33/86*     (2006.01)
    *G01N 21/82*     (2006.01)
    *G01N 35/04*     (2006.01)
    *G01N 15/06*     (2006.01)
    *G01N 21/25*     (2006.01)
    *G01N 21/15*     (2006.01)

(52) U.S. Cl.
    CPC ... *G01N2021/157* (2013.01); *G01N 2021/825* (2013.01); *G01N 2035/0441* (2013.01); *G01N 2035/0443* (2013.01); *G01N 2201/0256* (2013.01); *G01N 2201/04* (2013.01); *G01N 2201/0415* (2013.01); *G01N 2201/061* (2013.01); *G01N 2201/12723* (2013.01)

(56) References Cited

U.S. PATENT DOCUMENTS

| | | | |
|---|---|---|---|
| 6,734,021 B1 * | 5/2004 | Saito | G01N 33/18 422/82.01 |
| 2008/0044912 A1 | 2/2008 | Yamamoto et al. | |
| 2010/0130732 A1 * | 5/2010 | Chung | B01L 3/502738 536/25.41 |
| 2011/0008880 A1 * | 1/2011 | Uehata | G01N 35/00029 435/288.7 |

FOREIGN PATENT DOCUMENTS

| | | |
|---|---|---|
| JP | 08-114541 A | 5/1996 |
| JP | 2001-165937 A | 6/2001 |
| JP | 2008-046031 A | 2/2008 |

\* cited by examiner

AUTOMATIC ANALYSIS APPARATUS

TECHNICAL FIELD

The present invention relates: to an automatic analysis apparatus to automatically analyze a biological sample component such as blood; and in particular to a method for confirming an output light quantity of a scattered light source used for blood coagulation measurement and the like.

BACKGROUND ART

In an automatic analysis apparatus that measures on the basis of scattered light quantity change caused by blood coagulation and the like, a reaction liquid is irradiated with light and measured. In a light source however, it sometimes happens that a light quantity reduces by usage conditions, aging, dirt, and so on. Consequently, various methods for confirming a light quantity are adopted in conformity with apparatuses. Further, in blood coagulation measurement of a type based on scattered light measurement, a configuration of arranging a detector at an angle of about 90° to a light source and receiving scattered light is generally adopted and an apparatus having measurement sections at multiple places for increasing processing ability is the main stream. Furthermore, reaction containers are non-reusable in many blood coagulation items and a reaction container transfer mechanism to place and discard reaction containers is installed.

Meanwhile, in recent years an automatic analysis apparatus is required to be an apparatus capable of downsizing, low cost, high reliability, and high processing ability. With regard to the confirmation of the variation of a light source light quantity too, downsizing, low cost, high reliability, and others are required likewise.

In Patent Literature 1, a configuration of arranging a light source under a reaction container and two detectors laterally is disclosed. Further, a technology of installing a detector to compensate a light quantity variation portion laterally to a light source is disclosed.

Further, in Patent Literature 2, a technology of placing a light source beside a reaction container and installing a photodetector in a direction perpendicular to the incident direction of measurement light is disclosed.

CITATION LIST

Patent Literature

Patent Literature 1: Japanese Published Unexamined Application No. S59-28642
Patent Literature 2: Japanese Published Unexamined Application No. 2001-165937

SUMMARY OF INVENTION

Technical Problem

In the technology of Patent Literature 1, a detector for checking a light quantity has to be installed for each light source and, when a plurality of light sources are present, the problem is that detectors for checking light quantities of a number equal to the light sources are necessary, the apparatus configuration gets complex, and the apparatus becomes costly. Further, the technology of Patent Literature 2 is a method of projecting light from a side of a reaction container, whole agglutination reaction cannot be measured in the case of this method, and hence blood agglutination reaction measurement comes to be uneven due to the unevenness of agglutination reaction such as blood coagulation.

Solution to Problem

The representative features of the present invention are as follows.

(1) The present invention is an automatic analysis apparatus provided with: a plurality of detection sections, each of which has a reaction container installation section in which a reaction container in which a sample and a reagent react is placed; a light source being installed at the bottom of the reaction container installation section and projecting light; a first detector being installed in the reaction container installation section and detecting the light scattered from the reaction container in the light projected from the light source; a reaction container transfer mechanism being used commonly for the detection sections and holding, transferring, and placing the reaction containers; and a second detector being installed in the reaction container transfer mechanism and detecting the light projected from the light sources.

(2) In an automatic analysis apparatus according to the item (1), the automatic analysis apparatus is provided with a control section to raise an alarm stating that the light quantity of the light source is insufficient or facilitating the exchange of the light source when the light quantity detected with the second detector is smaller than a predetermined threshold value.

(3) In an automatic analysis apparatus according to the item (1) or (2): the automatic analysis apparatus is provided with an auxiliary tool of a material and a shape making it possible to detect the light projected from the light source and shield light from exterior; and the auxiliary tool is held by the reaction container transfer mechanism, is transferred above the light source, and detects the light projected from the light source with the second detector in the state of shielding the light from the exterior.

(4) In an automatic analysis apparatus according to any one of items (1) to (3): an empty reaction container is placed in the reaction container installation section; and an alarm stating that the empty reaction container has an abnormality is raised when the light quantity detected with the second detector in the light having been transmitted through the empty reaction container is smaller than a predetermined second threshold value.

(5) In an automatic analysis apparatus according to any one of the items (1) to (4), the drive of the reaction container transfer mechanism in the horizontal direction stops on the basis of the light quantity detected with the second detector.

Advantageous Effects of Invention

The present invention makes it possible to: eliminate the need for detectors for checking light quantities of a number equal to light sources; avoid the complexity of an apparatus configuration; and provide an inexpensive automatic analysis apparatus. Further, by commonly using a detector for checking a light quantity, it is possible to reduce variation between detectors. Furthermore, by installing a light source at the bottom of a reaction container installation section, it is possible to measure whole agglutination reaction, suppress the unevenness of blood agglutination reaction measurement caused by the unevenness of agglutination reaction such as blood coagulation, and obtain a highly accurate measurement result.

DESCRIPTION OF EMBODIMENTS

Figure 1:
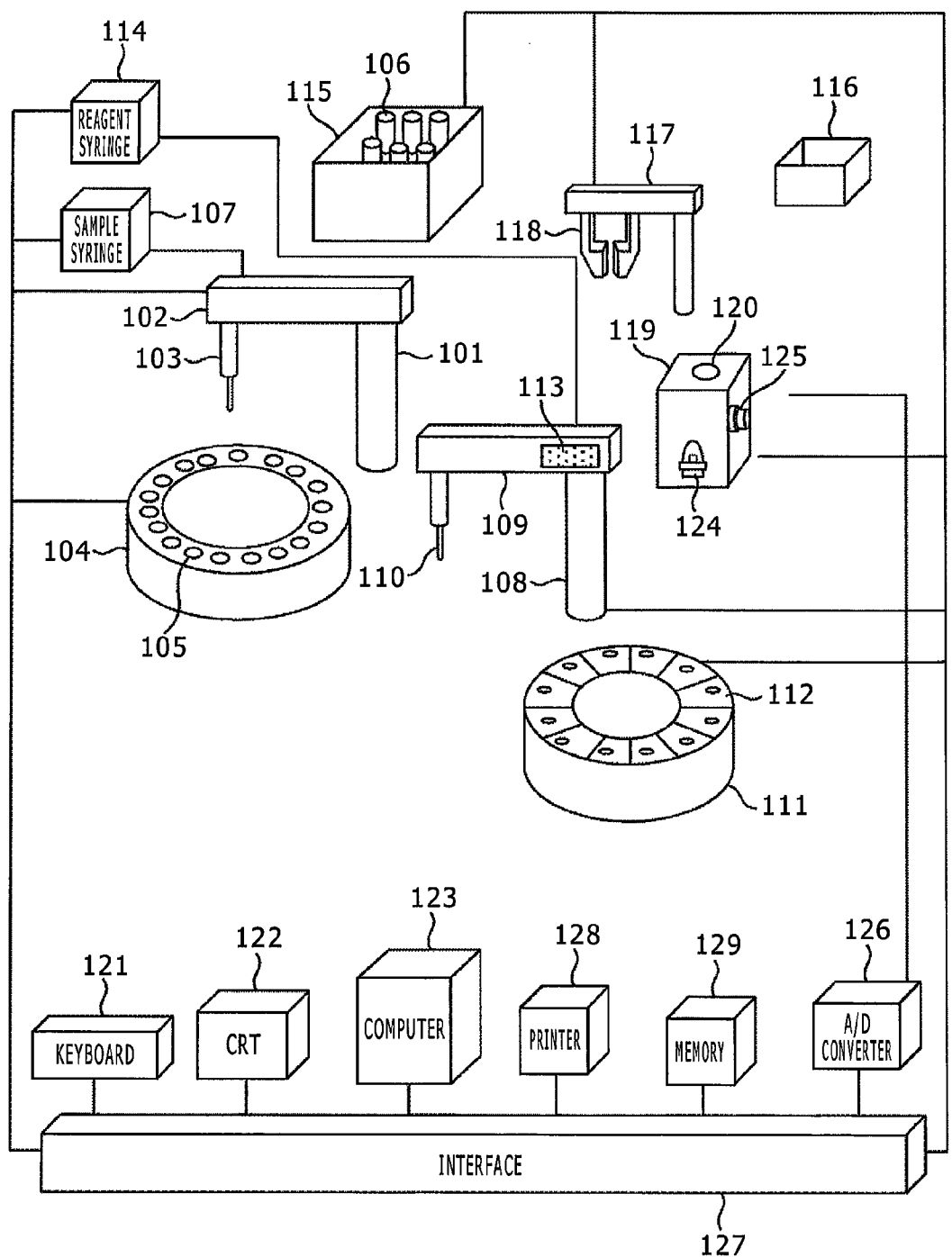
FIG. 1 is a schematic view of a general blood coagulation automatic analysis apparatus.

FIG. 1 is an example of a general blood coagulation apparatus configuration. The function of each section is publicly known and hence detailed descriptions are omitted. A sampling mechanism 101 is configured so that: a sampling arm 102 moves vertically and rotatably; and a sample dispensing probe 103 attached to the sampling arm 102 sucks a sample in a sample container 105 placed in a sample disk 104 rotating horizontally and discharges the sample to a reaction container 106. The sample dispensing probe 103 carries out the operations of sucking and discharging a sample in response to the operation of a sample syringe pump 107. Likewise, a reagent dispensing mechanism 108 is configured so that: a reagent dispensing arm 109 moves vertically and rotatably; a reagent dispensing probe 110 sucks a reagent in a reagent container 112 placed in a reagent disk 111 and discharges the sample to a reaction container 106; and a reagent heating mechanism 113 is incorporated in the interior. A sample and a reagent discharged to a reaction container 106 react. The reagent dispensing probe 110 carries out the operations of sucking and discharging a reagent in response to the operation of a reagent syringe pump 114. A reaction container 106 is retained by a reaction container retaining section 118 of a rotating reaction container transfer mechanism 117, moves rotatably from a reaction container supply section 115, and is placed in a reaction container installation section 120 of a detection section 119. The reaction container installation section 120 has a recess so as to be able to place a reaction container 106 and the reaction container 106 can be inserted into the recess. Here, two or more reaction container installation sections 120 are installed although it is not shown in the figure and the present apparatus has a plurality of detection sections 119. The reaction container transfer mechanism 117 is a mechanism used commonly for the detection sections and holds, transfers, and places a reaction container 106.

The flow of measurement is explained hereunder. Firstly, analysis items to be analyzed for each sample are inputted from an input device such as a keyboard 121 or the screen of a CRT 122. The operation of the unit is controlled by a computer (control section) 123. By the sampling mechanism 101, a sample in a sample container 105 placed in the sample disk 104 is sucked and dispensed to a reaction container 106 placed in the reaction container installation section 120 in the detection section 119. Successively likewise, by the reagent dispensing mechanism 108, a reagent is sucked from a reagent container 112 placed in the reagent disk 111, heated to an appropriate temperature by the reagent heating mechanism 113, and dispensed to the reaction container 106. Blood coagulation reaction starts promptly by the reagent discharge pressure. Light from the light source 124 is projected to the reaction container 106, the light scattered by a reaction solution in the reaction container is detected with the detector 125 such as a photodiode, a photometric signal enters the computer (control section) 123 via an interface 127 through an A/D converter 126, and coagulation reaction time is computed. The result is, through the interface 127, outputted by printing with a printer 128 or outputted on the screen of the CRT 122 and stored in a hard disk as a memory 129. The reaction container 106 after finishing the photometry is retained by the reaction container transfer mechanism 117 and discarded to a reaction container disposal section 116.

Figure 2:
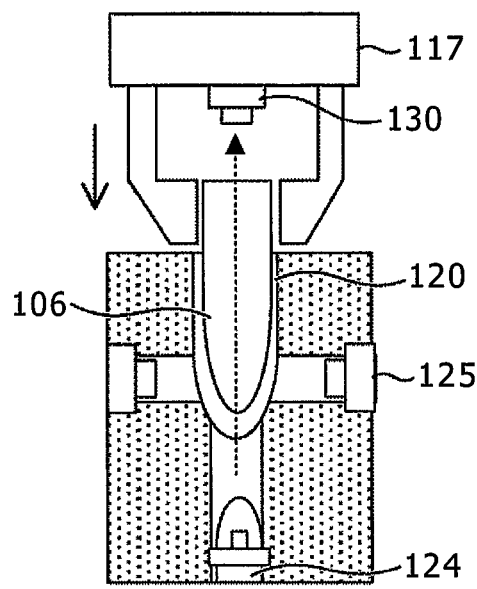
FIG. 2 is a representative example of the present invention.

FIG. 2 is a view explaining a reaction container transfer mechanism and a mechanism related to checking a light source light quantity according to the present invention. A light source 124 is installed at the bottom of a reaction container installation section 120 and a detector 125 to detect the light scattered from a reaction container in the light projected from the light source 124 is installed. For example, the detector 125 is installed on a side and in a recess of the reaction container installation section 120 as shown in the figure. Here, FIG. 2 shows the case of installing two detectors. A reaction container transfer mechanism 117 holds a reaction container 106, inserts the reaction container 106 into a recess of the reaction container installation section 120 while descending, and places the reaction container 106. A detector 130 for checking a light source light quantity to detect the light projected from the light source 124 is installed in the reaction container transfer mechanism 117. The detector 130 is installed at the root of two hold arms to hold the reaction container 106 of the reaction container transfer mechanism 117 so as to be able to detect light in FIG. 2 but the detector 130 may not necessarily be installed at the position as long as the detector 130 can detect the light projected from the light source 124.

When a light source light quantity is checked, the reaction container transfer mechanism 117, in the same manner as the operation at the time of reaction container supply, moves over the top face of the reaction container installation section 120 of the detection section 119 while either holding or not holding the reaction container and detects the light from the light source 124 with the detector 130 for checking a light source light quantity. On this occasion, when the light quantity detected by the detector 130 is smaller than a predetermined threshold value, the computer (control section) 123 raises an alarm stating that the light source is insufficient through the interface 127. Otherwise, the computer (control section) 123, through the interface 127, raises warning such as an alarm showing the abnormality of a light quantity and facilitates the exchange of the light source or raises an alarm facilitating the confirmation of the light source. In this way, an operator can recognize light source abnormality, light quantity abnormality, etc.

Meanwhile, the detector 130 for checking a light source light quantity can be used for positioning the reaction container transfer mechanism 117 in the horizontal direction in addition to the purpose of checking a light source light quantity. The computer (control section) 123 controls the reaction container transfer mechanism 117 so as to stop moving in the horizontal direction on the basis of the light quantity detected with the detector 130 and thereby the light quantity from the light source can be detected at a nearly identical position every time. For example, by controlling the reaction container transfer mechanism 117 so as to stop at a threshold value lower than the threshold value for light quantity check, the reaction container transfer mechanism 117 can stop at a nearly identical position regardless of a deteriorated state even when the output of the light source deteriorates. As a result, the computer (control section) 123 can recognize that the reaction container transfer mechanism 117 has reached immediately above the reaction container installation section 120 and it is possible to insert the reaction container into the recess accurately, hold the reaction container, and check the light quantity at a nearly identical position.

Figure 3:
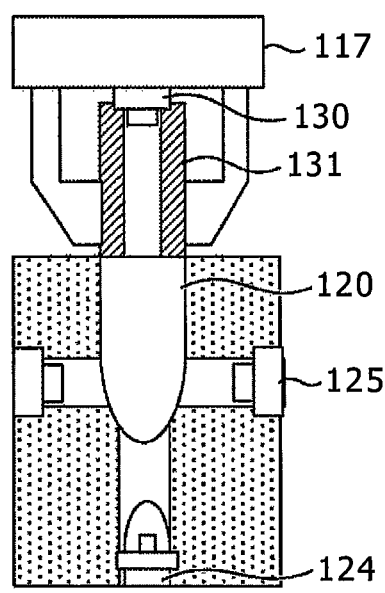
FIG. 3 is an example of using an auxiliary tool for detecting the variation of a light source light quantity.

FIG. 3 is the case of using an auxiliary tool 131 when the light quantity of the light source 124 is checked. When a light quantity is checked, an auxiliary tool 131 for light quantity check comprising a material that does not transmit light is held by the reaction container transfer mechanism 117 and installed at the reaction container installation section 120 and light is received through the auxiliary tool 131. That is, the auxiliary tool 131 is only required to: be able to detect light projected from the light source 124; and comprise a material and have a shape allowing light from exterior to be shielded. For example, the auxiliary tool 131 may comprise black resin having a cylindrical shape. The auxiliary tool 131 shown in the figure is only an example and the shape may not be cylindrical as long as the shape can effectively take in light source light. The auxiliary tool makes it possible to prevent noises caused by external light from being detected and check a light quantity accurately. The auxiliary tool 131 may also be configured so as to be always prepared in the reaction container supply section 115 and transferred from the reaction container supply section 115 to the reaction container installation section 120 by the reaction container transfer mechanism 117 in response to the request of light quantity check.

An example of a method for confirmation when a flaw or dirt exists in a reaction container is explained hereunder (refer to FIG. 1). The light quantity of the light source 124 is confirmed by the detector 130 for checking a light source light quantity or the like and that the light source has no abnormality is confirmed beforehand. When a reaction container is placed, the detector 130 for checking a light source light quantity detects the light source light having been transmitted through an empty reaction container and, if the light quantity is smaller than a predetermined threshold value, an alarm stating that the empty reaction container has an abnormality is raised or an alarm of indicating the exchange of the reaction container or the like is raised. In this way, by confirming that the light source does not have an abnormality beforehand, then placing an empty reaction container in the reaction container installation section 120, and detecting the light having been transmitted through the reaction container with the detector 130, it is possible to detect abnormality such as a flaw or dirt of the reaction container.

The present invention has heretofore been explained. The present invention makes it possible to provide a less expensive automatic analysis apparatus that can avoid the complexity of the apparatus configuration by using a detector 130 for checking a light source light quantity used commonly for a plurality of detection sections 119. Further, the present invention makes it possible to reduce variation between detectors. Furthermore, by installing a light source at the bottom of a reaction container installation section, it is possible to measure whole agglutination reaction, suppress the unevenness of blood agglutination reaction measurement caused by the unevenness of agglutination reaction such as blood coagulation, and obtain a highly accurate measurement result.

LIST OF REFERENCE SIGNS

101 Sampling mechanism
102 Sampling arm
103 Sample dispensing probe
104 Sample disk
105 Sample container
106 Reaction container
107 Sample syringe pump
108 Reagent dispensing mechanism
109 Reagent dispensing arm
110 Reagent dispensing probe
111 Reagent disk
112 Reagent container
113 Reagent heating mechanism
114 Reagent syringe pump
115 Reaction container supply section
116 Reaction container disposal section
117 Reaction container transfer mechanism
118 Reaction container retaining section
119 Detection section
120 Reaction container installation section
121 Keyboard
122 CRT
123 Computer (control section)
124 Light source
125 Detector
126 A/D converter
127 Interface
128 Printer
129 Memory
131 Auxiliary tool

The invention claimed is:

1. An automatic analysis apparatus comprising:
a control section;
a reaction container supply section holding a plurality of reaction containers;
a plurality of detection sections, each of which has a reaction container installation section in which a respective reaction container of the plurality of reaction containers is placed;
a respective light source installed in a bottom surface of the reaction container installation section in each of the detection sections for projecting light;
a first detector installed in the reaction container installation section in each of the detection sections and positioned out of optical alignment with the light source to detect light scattered from the reaction container of the light projected from the light source;
a reaction container transfer mechanism configured to be used commonly for the plurality of detection sections and for holding, transferring, and placing respective reaction containers of the plurality of reaction containers in each of the detection sections; and
one second detector installed in the reaction container transfer mechanism, configured to be used commonly for the plurality of detection sections and positioned to detect the light projected from each respective light source without the light passing through the reaction container,
wherein the control section is connected to the reaction container transfer mechanism, the first detector, and the second detector, and the control section is programmed to:
cause the reaction container transfer mechanism to move the second detector relative to the plurality of detection sections and to position the second detector above and in optical alignment with the light source in the respective reaction container installation sections,
cause the second detector to detect the light projected from the light source, cause the reaction container transfer mechanism to transfer a reaction container of the plurality of reaction containers to a detection section of the plurality of detection sections and place the reaction container in the reaction container installation section of the detection section, cause the first detector to detect light scattered from a reaction container that is placed in a reaction container installation section of a respective detection section, and analyze the scattered light to obtain an analysis result.

2. The automatic analysis apparatus according to claim 1, wherein the control section is programmed to raise an alarm indicating that the light quantity of the light source is insufficient before the reaction container is placed in the reaction container installation section when the light quantity detected with the second detector is smaller than a first predetermined threshold value.

3. The automatic analysis apparatus according to claim 2, further comprising an auxiliary tool of a material and a shape enabling detection of the light projected from the light source and shielding light from exterior, wherein the auxiliary tool is configured to be held by the reaction container transfer mechanism for being transferred above the light source, and enables detection of the light projected from the light source with the second detector in the state of shielding the light from the exterior.

4. The automatic analysis apparatus according to claim 2, wherein the control section is programmed to raise an alarm indicating that the reaction container has an abnormality if the light quantity detected with the second detector in the light transmitted through the reaction container is smaller than a predetermined second threshold value.

5. The automatic analysis apparatus according to claim 2, wherein the control section is programmed to stop the movement of the reaction container transfer mechanism in a horizontal direction based at least in part on the light quantity detected with the second detector.

6. The automatic analysis apparatus according to claim 1, wherein an auxiliary tool of a material and a shape making it possible to detect the light projected from the light source and shield light from exterior is held by the reaction container transfer mechanism, wherein the control section is programmed to:

cause the reaction container transfer mechanism that is holding the auxiliary tool to move to the plurality of detection sections and to position the second detector above the light source in the respective reaction container installation sections, and cause the second detector to detect the light projected form the light source.

7. The automatic analysis apparatus according to claim 6, wherein the control section is programmed to raise an alarm indicating that the reaction container has an abnormality if the light quantity detected with the second detector in the light transmitted through the reaction container is smaller than a predetermined threshold value.

8. The automatic analysis apparatus according to claim 6, wherein the control section is programmed to stop the movement of the reaction container transfer mechanism in a horizontal direction based at least in part on the light quantity detected with the second detector.

9. The automatic analysis apparatus according to claim 1, wherein the second detector is configured to detect the light projected from the light source when a reaction container is disposed in the reaction container installation section, and wherein the control section is programmed to raise an alarm indicating that the reaction container has an abnormality if the light quantity detected with the second detector in the light transmitted through the reaction container is smaller than a predetermined threshold value.

10. The automatic analysis apparatus according to claim 9, wherein the control section is programmed to stop the movement of the reaction container transfer mechanism in a horizontal direction based at least in part on the light quantity detected with the second detector.

11. The automatic analysis apparatus according to claim 1, wherein the control section is programmed to stop the movement of the reaction container transfer mechanism in a horizontal direction based at least in part on the light quantity detected with the second detector.

\* \* \* \* \*